US008940544B2

(12) United States Patent
Suri et al.

(10) Patent No.: US 8,940,544 B2
(45) Date of Patent: Jan. 27, 2015

(54) ANTIOXIDANT PROTECTION OF A CHEMICAL SENSOR

(75) Inventors: Jeff T. Suri, Rancho Santa Margarita, CA (US); Ritchie A. Wessling, Watsonville, CA (US); Thomas A. Peyser, Menlo Park, CA (US); Soya Gamsey, Huntington Beach, CA (US); Eric E. Patterson, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 494 days.

(21) Appl. No.: 13/022,494

(22) Filed: Feb. 7, 2011

(65) Prior Publication Data
US 2011/0236989 A1  Sep. 29, 2011

Related U.S. Application Data

(60) Provisional application No. 61/302,470, filed on Feb. 8, 2010.

(51) Int. Cl.
  *G01N 21/76* (2006.01)
  *G01N 21/64* (2006.01)
  *G01N 21/77* (2006.01)

(52) U.S. Cl.
  CPC ............ *G01N 21/6428* (2013.01); *G01N 21/77* (2013.01); *G01N 21/6408* (2013.01); *G01N 2021/6432* (2013.01); *G01N 2021/6484* (2013.01); *G01N 2021/773* (2013.01); *G01N 2021/7786* (2013.01)
  USPC ...................... 436/172; 422/82.05; 422/82.08

(58) Field of Classification Search
  None
  See application file for complete search history.

(56) References Cited

U.S. PATENT DOCUMENTS

| 6,254,829 B1 * | 7/2001 | Hartmann et al. .......... 422/82.06 |
| 6,858,403 B2 * | 2/2005 | Han et al. ........................ 435/27 |
| 2005/0048121 A1 | 3/2005 | East et al. |
| 2005/0173245 A1 | 8/2005 | Feldman et al. |
| 2007/0014726 A1 * | 1/2007 | Merical et al. ................. 424/9.1 |

FOREIGN PATENT DOCUMENTS

| WO | WO 01/20019 A2 | 3/2001 |
| WO | WO 2007/059311 A2 | 5/2007 |
| WO | WO 2007/067743 A2 | 6/2007 |
| WO | WO 2008/141241 A1 | 11/2008 |
| WO | WO 2010/123972 A1 | 10/2010 |

OTHER PUBLICATIONS

Hunneche, C.S. et al. Antioxidant activity of a combinatorial lirary of emulsifier-antioxidant bioconjugates, 2008, Journal of Agricultural and Food Chemistry, vol. 56(19), pp. 9258-9268.*

(Continued)

*Primary Examiner* — Robert Xu
(74) *Attorney, Agent, or Firm* — Medtronic Minimed, Inc.

(57) ABSTRACT

Analyte sensors having antioxidant protection are disclosed. By combining antioxidant and/or scavenger agents into polymer matrices that contain sensor moieties, the sensor moieties are protected from reactive oxygen species. Also disclosed are methods of making analyte sensors and methods of inhibiting oxidative degradation of sensing components in hydrated, polymerized analyte sensor systems.

18 Claims, 3 Drawing Sheets

(56) References Cited

OTHER PUBLICATIONS

Gamsey, S. et al. Continuous glucose detection using boronic acid-substituted viologens in fluorescent hydrogels: linker effects and extension to fiber optics, 2006, Langmuir, vol. 22(21), pp. 9067-9074.*

Suri, J.T. et al. 2003 "Continuous glucose sensing with a fluorescent thin-film hydrogel" *Angew Chem Int Ed* 42:5857-5859.

* cited by examiner

ANTIOXIDANT PROTECTION OF A CHEMICAL SENSOR

RELATED APPLICATIONS

This application claims the benefit of U.S. Provisional Application No. 61/302,470 filed Feb. 8, 2010, which is hereby incorporated by reference in its entirety.

FIELD OF THE INVENTION

The present invention relates to analyte sensors, including equilibrium fluorescence indicator systems having antioxidant protection.

DESCRIPTION OF THE RELATED ART

Investigators have used fluorescent techniques to measure the concentration of analyte compounds (e.g., glucose) in body fluids. For example, Russell, disclosed the use of a boronic acid functionalized dye that binds to glucose and generates a signal dependent on glucose concentration (U.S. Pat. No. 5,512,246). James et al. used the same principle but combined a fluorescent dye, an amine quenching functionality, and a boronic acid in a single complex moiety, the fluorescence emission from which varies with the extent of glucose binding (U.S. Pat. No. 5,503,770). Glucose sensors comprising a fluorescent dye and a quencher comprising a single viologen moiety appended with boronic acids have been synthesized and investigated (e.g., U.S. Pat. Nos. 6,627,177, 6,653,141, and 7,470,420; Suri, J. et al. 2003 *Angew Chem Int Ed Engl* 42:5857-5859; Gamsey, S. et al. 2006 *Langmuir* 22:9067-9074; Thoniyot, P. et al. 2006 *Diabetes Technol Ther* 8:279-287; Cordes, D. B. et al. 2005 *Langmuir* 21:6540-6547; Cordes, D. B. et al. 2005 *Org Biomol Chem* 3:1708-1713; Cappuccio, E. E. et al. 2004 *J Fluoresc* 14:521-533; Gamsey, S. et al. 2007 *J Am Chem Soc* 129:1278-1286 and Cordes, D. B. et al. 2006 *Angew Chem Int Ed Engl* 45:3829-3832).

Fluorescent dyes, including 8-hydroxypyrene-1,3,6-trisulfonic acid (HPTS) and its derivatives, are known and have been used in analyte detection. See, e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; International Application No. PCT/US2003/030167; and co-pending U.S. patent application Ser. Nos. 10/456,895 and 11/296,898.

Catalase enzymes catalyze the conversion of hydrogen peroxide ($H_2O_2$) to oxygen ($O_2$) and water ($H_2O$) (Zamocky, M. et al. 2008 *Antioxid Redox Signal* 10:1527-1548; Chelikani, P, et al. 2004 *Cell Mol Life Sci* 61: 192-208). Catalase enzyme has been used in biosensor hydrogels to remove hydrogen peroxide (e.g., WO 01/75089 and U.S. Pat. No. 6,858,403). In WO 01/75089, the catalase enzyme was shown to provide improved hydrogels that have much faster swelling response times as compared to hydrogels without catalase. Such biosensors employed an immobilized analyte-sensitive enzyme, which had an increased useful life due to protection from degradation by hydrogen peroxide of the immobilized analyte-sensitive enzyme. In U.S. Pat. No. 6,858,403, hydrogels containing catalase co-immobilized with glucose oxidase had an increased useful life due to protection of the immobilize analyte-sensitive enzyme from degradation by hydrogen peroxide. Catalase has been used to scavenge $H_2O_2$ from contact lens solutions (U.S. Pat. No. 5,521,091) and from disinfectant solutions (U.S. Pat. No. 4,829,001) where it was immobilized on a solid support. Synthetic, catalytic antioxidant molecules have been reported to reduce or prevent oxidative damage to indicator macromolecules in biosensors (U.S. Application Publication No. 2007/0014726).

The use of noble metals and metal oxides to decompose $H_2O_2$ has been known for many years (Maggs & Sutton 1958 *Trans Faraday Soc* 54:1861-1870; U.S. Pat. No. 3,423,330; and McKee, D. W. 1969 *J Catalysis* 14:355-364). However, no one has shown or suggested that metals and their oxides can be used to protect fluorescence-based sensors from oxidative degradation.

SUMMARY OF THE INVENTION

An analyte sensor is disclosed, comprising an equilibrium fluorescence indicator system and at least one antioxidant, wherein each of the equilibrium fluorescence indicator system and the at least one antioxidant is immobilized within a polymer matrix.

In one variation to the analyte sensor, the equilibrium fluorescence indicator system and the at least one antioxidant is immobilized within a common polymer matrix. In another variation, the equilibrium fluorescence indicator system is immobilized within a first polymer matrix and the at least one antioxidant is immobilized within a second polymer matrix that forms an exterior coating around the first polymer matrix. In yet another variation, the analyte sensor may further comprise a second polymer matrix that comprises at least one antioxidant, wherein the second polymer matrix forms an external coating around the common polymer matrix within which the equilibrium fluorescence indicator system and at least one antioxidant is immobilized.

The at least one antioxidant may be selected from the group consisting of a catalytic antioxidant molecule, a scavenger molecule and a synthetic antioxidant molecule. The catalytic antioxidant may be selected from the group consisting of catalase (CAT), glutathione peroxidase (GSH-Px), selenium glutathione peroxidase and superoxide dismutase (SOD). Alternatively, the catalytic antioxidant may be selected from the group consisting of bioconjugates of catalase (CAT), glutathione peroxidase (GSH-Px), selenium glutathione peroxidase and superoxide dismutase (SOD). The synthetic antioxidant molecule may be TEMPOL. The scavenger antioxidant molecule may be selected from the group consisting of vitamin A, a retinol, a carotenoid, a limonoid, a phytosterol, a flavonoid, an anthocyanidin, a catechin, an isoflavone, an oligomeric proanthocyanidin, an isothiocyanate, a dithiolthione, a sulforaphane, an isoprenoid, a tocotrienol, a tocopherol, vitamin E, lipoic acid, ubiquinone, an ascorbate, vitamin C, 2,3-dihydro-1-benzofuran-5-ols, a chromanone, a water-soluble fullerene antioxidant, C60, C70, a phenolic antioxidant compound such as butylated hydroxytoluene (BHT) and Trolox™; a polyphenolic antioxidant compound such as caffeic acid, hydrocaffeic acid, cinnamic acid, benzoic acid and vanillic acid; and pyruvate. In one preferred embodiment, the synthetic antioxidant molecule is a porphyrin-based synthetic antioxidant molecule. In another preferred embodiment, the synthetic antioxidant is a noble metal, such as platinum, palladium, silver, or gold, and alloys thereof, or a metal oxide or sulfide selected from the group consisting of manganese dioxide, ruthenium oxide, ruthenium sulfide, and silver oxide, Preferably the synthetic antioxidants are in the form of porous coatings or colloidal particles including nanoparticles, of silver oxide, and nanoparticles of platinum, silver, or gold.

In another variation to the analyte sensor, the at least one antioxidant component may comprise a cocktail of two or more antioxidants. The two or more antioxidants may be a catalase and an antioxidant phenolic compound. The antioxidant phenolic compound may be Trolox™ or a Trolox™ derivative. The two or more antioxidants may also be a catalase enzyme and vitamin E.

In embodiments of the analyte sensor comprising first and second polymer matrices, these may be physically separated by a semi-permeable membrane.

In another embodiment, an analyte sensor is disclosed comprising an equilibrium fluorescence indicator system immobilized within an insoluble polymer matrix and a porous metal coating surrounding said insoluble polymer matrix.

In another embodiment, an analyte sensor comprises an equilibrium fluorescence indicator system and at least one antioxidant, wherein the equilibrium fluorescence indicator is immobilized within a polymer matrix and the at least one antioxidant is covalently bound to a semi-permeable membrane that surrounds the polymer matrix.

In another embodiment, an analyte sensor is disclosed comprising: an optical fiber with proximal and distal ends; a chemical indicator system capable of generating an emission light signal in response to an excitation light signal, wherein the intensity of the emission light signal is related to the analyte concentration, and wherein the chemical indicator system is immobilized within a gap in the optical fiber by a polymer matrix; a selectively permeable membrane disposed over the gap; and an external coating that contains one or more antioxidant, wherein the sensor is preferably sized for deployment within a blood vessel.

In a preferred variation, the analyte is glucose and the chemical indicator system comprises a fluorophore operably coupled to a glucose binding moiety, wherein glucose binding causes an apparent optical change in the fluorophore.

A method of making an analyte sensor is disclosed comprising immobilizing an equilibrium fluorescence indicator system and at least one antioxidant within a common polymer matrix.

Another method of making an analyte sensor is disclosed comprising immobilizing an equilibrium fluorescence indicator system within an first polymer matrix; and immobilizing at least one antioxidant within a second polymer matrix, wherein the second polymer matrix forms an exterior coating around the first polymer matrix.

Another method of making an analyte sensor is disclosed comprising immobilizing an equilibrium fluorescence indicator system and at least one antioxidant within a first polymer matrix; and immobilizing at least one antioxidant in an second insoluble matrix, wherein the second polymer matrix forms an external coating around the first polymer matrix.

An analyte sensor is disclosed in accordance with another variation, wherein the equilibrium fluorescence indicator system comprises: a fluorescent, organic dye; a boronic acid functionalized viologen quencher; and a hydrogel matrix.

In one variation to the analyte sensor, the equilibrium fluorescence indicator system may be protected against degradation caused by hydrogen peroxide.

DETAILED DESCRIPTION OF THE PREFERRED EMBODIMENT

A protective antioxidant hydrogel is described herein that inhibits oxidative degradation of sensing components. This antioxidant hydrogel may be used in combination with analyte-binding moieties to achieve real-time measurement of analyte levels, providing stable operation for at least 8 hours, preferably greater than 24 hours.

DEFINITIONS

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

"Reactive oxygen species" or "ROS," as used herein refers to highly reactive and toxic oxygen compounds that are generated in the course of normal electron transport system during respiration or that are generated in a disease or during treatment with certain therapeutic agents for a particular disorder. ROS include, but are not limited to, the superoxide anion ($O_2.^-$), hydrogen peroxide ($H_2O_2$), singlet oxygen, lipid peroxides, and peroxynitrite.

"Reactive nitrogen species" or "RNS" as used herein refers to nitrogen-containing ions, free radicals as well as non-radical species. Some non-limiting examples of reactive nitrogen species include nitric oxide (NO.), nitrogen dioxide ($NO_2$.), nitrite ($NO_2^-$), and peroxynitrite ($ONOO^-$).

"Free radical," as used herein, refers to any atom or any molecule or compound that possesses an odd (unpaired) electron. By this definition, the superoxide anion is also considered a negatively charged free radical. One of the most common and potentially destructive types of free radical other than the superoxide anion is a hydroxyl radical. Typically, the generation of ROS, such as superoxide anion or singlet oxygen, also leads to one or more other harmful free radicals as well. Accordingly, phrases such as "ROS and free radicals" or "ROS and other free radicals," as used herein, are meant to encompass any or all reactive, oxidative molecular species or compounds that may be generated in a particular metabolic state or condition of cells and tissues of interest.

"Oxygen radical scavengers" or "lazaroids" are a class of compounds that have an ability to scavenge and detoxify ROS and free radicals. Vitamins A, C, E, and related antioxidant compounds, such as β-carotene and retinoids, are members of this large class of compounds, as are antioxidative enzymes, such as superoxide dismutase (SOD) and catalase (CAT), glutathione peroxidase (GSH-Px) and selenium glutathione peroxidase. In healthy individuals, sufficient levels of antioxidative enzymes and other lazaroids are present both intracellularly and extracellularly to efficiently scavenge sufficient amounts of ROS and free radicals to avoid significant oxidative damage to cells and tissues.

As used herein, an "antioxidant" is a substance that, when present in a mixture or structure containing an oxidizable substrate molecule, significantly delays or prevents oxidation of the substrate molecule. Antioxidants can act by scavenging reactive free radicals or other reactive oxygen species (e.g., $O_2.^-$, $H_2O_2$, HO., HOCl, ferryl, peroxyl, peroxynitryl, and alkoxyl), by preventing their formation, or by catalytically converting the free radical or other reactive oxygen species to a less reactive species. An antioxidant compound of the present invention may have detectable superoxide dismutase (SOD), catalase (CAT) and/or peroxidase (POD) activity. A compound of the present invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel assay reaction that is not treated with the compound. The relative amount of free radical species may be determined by detection of a secondary indicator (e.g., an oxidized substrate, peroxidized lipid, cytochrome C).

Analyte Sensor Degradation

Analyte sensors are degraded by the action of oxidative agents that are generated in vivo. The agents have a limited lifetime in vitro. Such degradation is not due to oxygen alone because an essentially unlimited supply of oxygen is present under all circumstances. Light is a factor, but is not essential because oxidizing agents or free radical attack can damage the sensor even in the dark.

Analyte sensors may also undergo self-induced degradation. For example, viologens are oxidizing agents that, under some circumstances, can generate superoxide and hydrogen peroxide by reaction with oxygen.

Reactive Oxygen Species

Reactive oxygen species (ROS) are prevalent in the human body and can occur as a result of injury, trauma, or other physiological processes. (Halliwell B and, Gutteridge J M C, Free Radicals in Biology and Medicine $4^{th}$ ed., Oxford University Press, 2007). These species are considered oxidative in nature and therefore contribute to what clinicians call "oxidative stress". There are two types of ROS, i.e., radical and non-radical. ROS in plasma, such as hydrogen peroxide, are capable of permeating though permeable membranes of sensing devices and interacting with sensing moieties. Such ROS must have certain characteristics. For example they must be soluble both in plasma and in a hydrogel medium. They must have a sufficiently long lifetime to allow transport out of cells into plasma and then into the illuminated region of a hydrogel containing sensing moieties. They may be activated by blue light, either alone or in concert with dye/quencher and/or oxygen. The effect is that modulation of the sensor is degraded. A likely cause is that some element(s) of the sensing chemistry is damaged either directly by reaction with the unknown agent, or by attack of a reactive intermediate (e.g., a radical).

A large number of ROS, reactive nitrogen species (RNS), and miscellaneous other reactive species exist in human blood plasma. Many of these are free radicals. Free radicals include superoxide, hydroxyl, hydroperoxyl, carbonate, carbon dioxide, chlorine, peroxyl, alkoxyl, nitric oxide, nitrogen dioxide, nitrate and singlet oxygen. In addition, there are sulfur radicals, typically formed from sulfhydryl and disulfide intermediates. Most of these radicals have very short life times in vivo. Notable exceptions are the radicals generated by oxidation of phenolic compounds; i.e., radicals formed by reaction of antioxidants with other ROS. These are resonance-stabilized radicals that probably would not themselves damage a sensor, but might participate in a sequence of reactions that does lead to damage.

Under circumstances where sensor degradation is due to radical attack, the radical is likely be generated locally; i.e., inside the sensor. A typical radical might diffuse a little faster than glucose, but not by orders of magnitude. Thus, to reach the illuminated region in the sensor it would have to survive for minutes. Long-term stability is unlikely for highly reactive species like hydroxyl. On the other hand, radicals that have long term stability are not very reactive. In any event, a radical involved in sensor degradation would need to exist in significant concentrations in equilibrium with all components that are present in plasma, and have a lifetime sufficient to permeate through the hydrogel-filled membrane pores. The reaction may also involve oxygen, photo-excitation, and metal ion catalysis.

A variety of non-radical ROS are known to be present in vivo. For example, non-radical ROS include hydrogen peroxide, peroxynitrite, peroxynitrous acid, nitrosoperoxycarbonate, hyochlorite/hypochlorous acid, ozone, singlet oxygen, organic peroxides and carbon dioxide adducts.

Hydrogen peroxide is a ROS that is potentially involved in sensor degradation. Hydrogen peroxide is normally present in blood plasma and the reported range for extracellular $H_2O_2$ is from 0.02 μM to 2 μM or higher. Enhanced levels of $H_2O_2$ are generated as a result of injury. $H_2O_2$ permeates readily through cell walls so that intracellular and extracellular concentrations can rapidly equilibrate. Hydrogen peroxide is not only an oxidant but is also involved in redox signaling (2009 Jacob, C. and Winyard, P. G. (eds) in *Redox Signaling and Regulation in Biology and Medicine*, John Wiley and Sons, Inc.-VCH). It is excreted by cells under normal conditions and at an accelerated rate under stress. $H_2O_2$ itself is not very reactive, giving it a long lifetime in biological media. Nevertheless, $H_2O_2$ can oxidize many molecules directly, or form more reactive hydroxyl radicals that can attack almost anything in the biological environment. Hydroxyl radicals can be generated by irradiating $H_2O_2$ with light from a 470 nm light emitting diode (LED). Finally, hydrogen peroxide has been shown to degrade the sensor (see FIG. 2).

Peroxynitrite is formed in vivo by reaction of superoxide with nitric oxide. Two recent reviews relate to the chemistry of peroxynitrite (Szabo, C. et al. 2007 "Peroxynitrite: biochemistry, pathophysiology, and development of therapeutics" *Nature Reviews (Drug Discovery)* 6:662-680 and Goldstein et al. 2005 "Chemistry of Peroxynitrites as Compared to Peroxynitrates" *Chem Rev* 105:2457-2470). Peroxynitrite is continuously generated intracellularly, but steady-state concentrations remain very low (in the nanomolar range) because of its very short lifetime in vivo (10 ms). Peroxynitrite is characterized as being both very stable and very reactive. Stability depends on pH. The anion is stable, but the free acid is not. At physiological pH, about 20% is free acid which decomposes rapidly. Peroxynitrous acid is soluble in lipids where it decomposes to hydroxyl and nitrogen dioxide radicals, which attack polyunsaturated acids.

Peroxynitrite permeates through cell walls and can be found in plasma. However, in aqueous media, it reacts rapidly with carbon dioxide to form carbonate radical ion, a highly reactive oxidizing radical with a very short lifetime (Augusto et al. 2002 Nitrogen dioxide and carbonate radical ion: Two emerging radicals in biology *Free Radical Biol Med* 32:841-859). Much of the damage in biological systems attributed to peroxynitrite is probably caused by carbonate radical. Peroxynitrite may not be likely to come in direct contact with the sensing components. Alternatively, its mechanism of action may be through the formation of radical derivatives outside of the sensor.

Hypochlorite/hypochlorous acid is an unlikely candidate for a role in analyte sensor degradation, even though it would be highly reactive with the sensing components. It is produced by reaction of $H_2O_2$ with chloride ion. While both $H_2O_2$ and chloride ion may diffuse into the sensor, the enzyme myeloperoxidase is required for this reaction to occur. However, it is highly unlikely that the enzyme is also present in the sensor. When hypochlorite is generated outside the sensor, the probability that it can last long enough to diffuse into the sensor is low.

Ozone is a strong, water soluble oxidant that could attack the sensing components. However, ozone is normally assumed to be exogenous, so it has an equal probability of being present either in vivo or in vitro.

Singlet oxygen is also a powerful, water-soluble oxidizing agent. It can be generated in vivo by photosensitized conversion of oxygen. Both oxygen and light are present in the sensor. Consequently, singlet oxygen formation is possible if a photosensitizer is also present. The fluorescence indicator system does not act as a photosensitizer because, if that were the case, degradation would also happen in a blood loop, which is not observed. The photosensitizer must be a small, relatively unstable molecule that is only present in plasma in vivo. Many biomolecules are known sensitizers for singlet oxygen formation.

Organic peroxides can be activated by transition metal ions or light to produce radicals, which could then attack the sensing components. Though these peroxides are probably present in plasma, they are associated with lipid bilayers and dispersed lipoproteins, which are unlikely to penetrate the sensor.

Carbon dioxide adducts, including peroxymonocarbonate and carbonate radical ion, are candidates of interest. Peroxymonocarbonate is formed by reaction of hydrogen peroxide and bicarbonate ion, both of which are present in the sensor. Peroxycarbonate is more reactive than $H_2O_2$ and could directly attack the sensing components. It can also generate carbonate radical ion, a highly reactive, oxidizing radical. Much less is known about the behavior of these molecules in vivo as compared to other ROS.

Iron in Analyte Sensor Degradation

Transition metal ion catalysis may also be involved in sensor degradation. Much of the chemistry of $H_2O_2$ is influenced by catalysis, especially by ferrous ions. If both $Fe^{2+}$ ions and $H_2O_2$ enter a sensor, the Fenton reaction can occur, generating hydroxyl radicals.

The destructive potential of iron ions in biological systems is controlled by chelation; i.e., in vivo iron is tied up in complexes that modulate its catalytic activity. Iron in plasma is rendered non-catalytic by being tightly bound to transferrin. Transferrin has a molecular weight of about 80 KDa, which is too high to allow permeation into the sensor. Accordingly, iron from this source does not pose a problem for the sensor. Free iron is usually defined as non-transferrin bound iron (NTBI). Several techniques for measuring NTBI have been reported (Jacobs et al. 2005 "Results of an international round robin for the quantification of serum non-transferrin-bound iron" *Anal Biochem* 341:241-250).

There is virtually no NTBI in healthy humans, but that is not the case for patients under stress. For example, NTBI is formed as a result of blood transfusions, a frequent occurrence in intensive care units of hospitals (Osment and Turly 2009 "Iron overload following red blood cell transfusion and its impact on disease severity" *Biochim Biophys Acta* 1790: 694-701). It is also associated with various diseases including diabetes (Rajpathak et al. 2009 "The role of iron in type 2 diabetes in humans" *Biochim Biophys Acta* 1790:671-681); and is found in cancer patients receiving chemotherapy (Kolb et al. 2009 "Non-transferrin bound iron measurement is influenced by chelator concentration" *Anal Biochem* 385:13-19). In general, there seems to be an association between NTBI and oxidative stress. In addition, there is a possibility that NTBI is generated at the site of a wound, as has been shown for hydrogen peroxide.

The presence of even very low levels of NTBI in plasma could lead to some getting into the sensor. Truly free Fe ions are thought to not exist in plasma; they have to be complexed in some fashion by other species present in plasma. In particular, free ferric ion would precipitate as the hydroxide at physiological pH. It is transported in blood as the transferrin complex. Possible non-protein complexing species in plasma include citrate and the various phosphates. A citrate complex would be able to permeate through the membrane.

A related issue is the effect of ascorbic acid on NTBI and its role in generating hydroxyl radical (Daurte and Jones 2007 "Vitamin C modulation of $H_2O_2$-induced damage and iron homeostasis in human cell" *Free Radical Biology Medicine* 43:1165-1175). Significant amounts of ascorbic acid are found in plasma. Therefore, it may also be present in the sensor. Ascorbic acid can reduce $Fe^{3+}$ to $Fe^{2+}$. Thus, if $H_2O_2$ is also present, and a ferric citrate complex gets into the sensor, this can result in formation of hydroxyl radicals.

Antioxidants

By combining antioxidant and/or scavenger agents into polymer matrices that contain sensor moieties, the sensor moieties are protected from ROS. A variety of naturally occurring, catalytic or scavenger antioxidants are known in the art. In addition, a variety of synthetic (mimetic), catalytic scavengers of reactive oxygen chemical species are known.

1. Natural

Biological antioxidants include well-defined, naturally occurring catalytic metalloenzymes, such as superoxide dismutase (SOD), catalase (CAT), and glutathione peroxidase (GSH-Px).

There are three general families of catalase proteins. Although catalyzing the same reaction (2H2O2→2H2O+ O2), the three groups differ significantly in their overall and active-site architecture and the mechanism of reaction. Two of the protein families are heme enzymes: typical catalases and catalase-peroxidases. Typical catalases catalyze the decomposition of hydrogen peroxide to water and oxygen and comprise the most abundant group found in Eubacteria, Archaeabacteria, Protista, Fungi, Plantae, and Animalia, whereas catalase-peroxidases are not found in plants and animals and exhibit both catalase and peroxidase activities. The third group is a minor bacterial protein family with a dimanganese active site called manganese catalases.

Superoxide dismutases are a ubiquitous family of enzymes that function to efficiently catalyze the dismutation of superoxide anions. The SOD-catalyzed dismutation of superoxide may be written with the following half-reactions: $M^{(n+1)+}-SOD+O_2^- \rightarrow M^{n+}-SOD+O_2$ and $M^{n+}-SOD+O_2^-+2H^+ \rightarrow M^{(n+1)+}-SOD+H_2O_2$, where M=Cu (n=1); Mn (n=2); Fe (n=2); Ni (n=2). Three unique and highly compartmentalized mammalian superoxide dismutases have been biochemically and molecularly characterized. SOD1, or CuZn-SOD, was the first enzyme to be characterized and is a copper and zinc-containing homodimer that is found almost exclusively in intracellular cytoplasmic spaces. SOD2, or Mn-SOD, exists as a tetramer and is initially synthesized containing a leader peptide, which targets this manganese-containing enzyme exclusively to the mitochondrial spaces. SOD3, or EC-SOD, exists as a copper and zinc-containing tetramer, and is synthesized containing a signal peptide that directs this enzyme exclusively to extracellular spaces.

Glutathione peroxidase (GPx) is the general name for a family of multiple isozymes that catalyze the reduction of $H_2O_2$ or organic hydroperoxides to water or corresponding alcohols using reduced glutathione (GSH) as an electron donor ($H_2O_2+2GSH \rightarrow GS-SG+2H_2O$). In Metazoa, some GPxs have a selenium-dependent glutathione peroxidase activity. In mammalian tissues, there are six selenium dependent GPx isozymes. In addition, a phospholipid hydroperoxide glutathione peroxidase (PHGPx) has been described in mammals, which incorporates cysteine instead of selenocysteine in the conserved catalytic motif. Glutathione peroxidases have been indentified in many organisms, including plants.

Natural scavenger molecules react with free radicals, notably peroxyl radicals, and with singlet molecular oxygen, becoming consumed in the process. Suitable free radical scavengers include vitamin A (which is a generic term that includes a number of molecules with the biological activity of retinol or carotenoids), limonoids, phytosterols, flavonoids, anthocyanidins, catechins, isoflavones, oligomeric proanthocyanidins, isothiocyanates, dithiolthiones, sulforaphane, isoprenoids, tocotrienols, tocopherols (e.g. vitamin E), lipoic acid, ubiquinone, ascorbates (e.g., vitamin C), 2,3-dihydro-1-benzofuran-5-ols, chromanones, water-soluble fullerenes including C60 and C70, phenolic compounds such as butylated hydroxytoluene (BHT), Trolox™, which is a water soluble derivative of vitamin E; and polyphenolic antioxidant compounds such as caffeic acid, hydrocaffeic acid, vanillic acid, cinnamic acid and benzoic acid; and pyruvate.

2. Synthetic Mimetics

Synthetic catalytic scavengers for reactive oxygen species may be used in various embodiments of the present invention. Such compounds are effective as superoxide dismutase and/or catalase and/or peroxidase mimetics, which have antioxidant and/or free radical scavenging properties and function in vivo as antioxidants. For example, synthetic, metalloporphyrin-based antioxidants are known in the art, e.g., as disclosed in WO 02/04454. These porphyrin-based antioxidants provide synthetic transition metal complexes that have the ability to scavenge reactive oxygen species.

Tempol (4-hydroxy-2,2,6,6-tetramethyl-1-piperidine-1-oxyl) is a low molecular weight, hydrophilic, metal-free, non-toxic nitroxide. Tempol works as a peroxidase and superoxide dismutase mimic. It inhibits lipid peroxidation and the Fenton reaction formation of hydroxyl radicals.

3. Iron Chelation

Only trace amounts of ferrous ion are needed to catalyze the Fenton reaction. Therefore, another approach to stabilizing the sensor, in addition to the use of antioxidants, is to include an iron-binding element. To be effective, an iron-binding element would likely have to be located inside the membrane, not on the surface. Attaching a polymerizable group to a known chelating agent that renders iron non-catalytic, and copolymerizing it into the hydrogel is one solution. Its practicality depends on how difficult the synthesis of a chelating monomer would be. One problem with this approach is that Fe ions in the sensor would be continually replenished by non-transferrin bound iron in plasma. Like the antioxidants, Vitamins E and C, the chelating agent would also be used up over time. Thus, its effectiveness depends on how long it takes to saturate with iron.

4. Metal and Metal Oxides

Metal and metal oxides may also be utilized as catalysts for conversion of hydrogen peroxide to water and oxygen. Non-limiting examples of metal and metal oxide catalysts include noble metals, such as platinum, palladium, silver, or gold, and alloys thereof, or a metal oxide or sulfide selected from the group consisting of manganese dioxide, ruthenium oxide, ruthenium sulfide, and silver oxide, Preferably the synthetic antioxidants are in the form of porous coatings or colloidal particles including nanoparticles, of silver oxide, and nanoparticles of platinum, silver, or gold. Silver has been used in hydrogels and in membranes (Thomas, V. et al. 2007 *J Colloid and Interface Science* 315:389-395; Mohan, Y. M. et al. 2006 *Macromol Rapid Commun* 27:1346-1354). Silver oxide catalysts were disclosed for decomposition of dilute hydrogen peroxide (U.S. Pat. No. 3,423,330). Silver-coated nylon fiber has been used as an antibacterial agent (MacKeen, P. et al. 1987 *Antimicrobial Agents and Chemotherapy* 31:93-99) and plastic catheters coated with silver nanoparticles were shown to have antimicrobial activity (Roe, D. et al. 2008 *J Antimicrobial Chemotherapy* 61:869-876). Rutheinum oxide and manganese dioxide were found to effectively scavenge hydrogen peroxide in a dialysis membrane (U.S. Pat. No. 3,996,141).

Configurations for Antioxidant Protection

Figure 1:
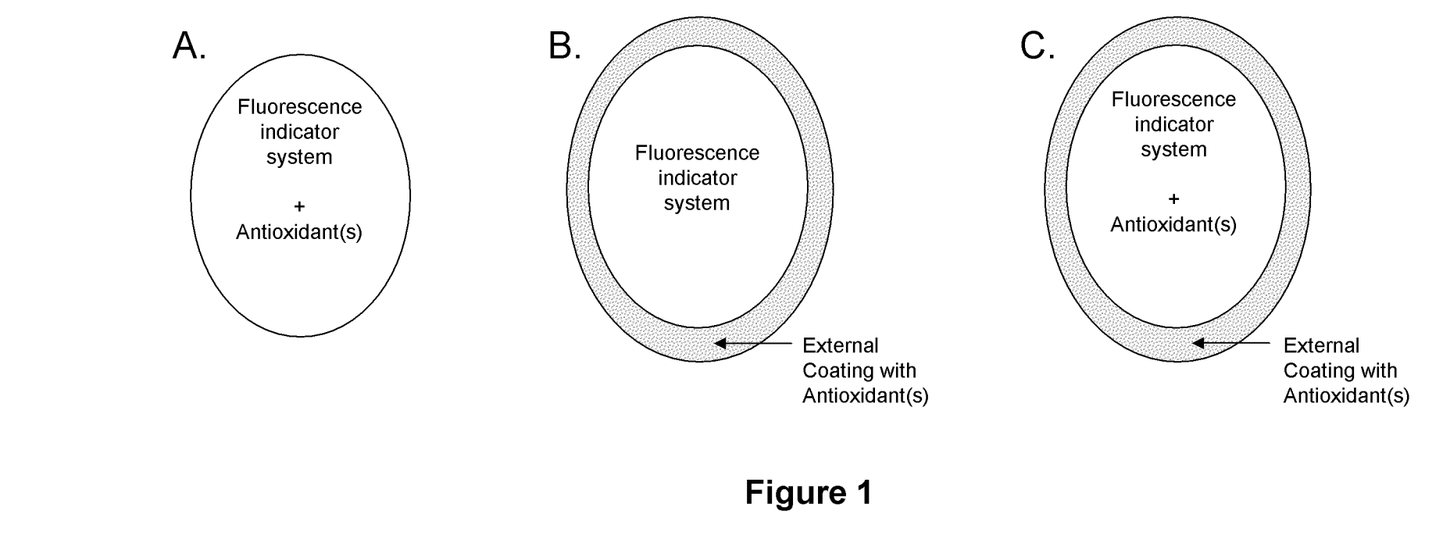
FIG. 1. Schematic diagrams of various sensor configurations. (A) An equilibrium fluorescence indicator system is combined together with one or more antioxidant within the same polymer matrix. (B) An equilibrium fluorescence indicator system is located in an internal polymer matrix and an exterior coating around the internal polymer matrix comprises at least one antioxidant. (C) An internal polymer matrix comprises an equilibrium fluorescence indicator system and one or more antioxidant and an exterior coating around the internal polymer matrix also comprises at least one antioxidant.

In some embodiments, an equilibrium fluorescence indicator system is combined together with one or more antioxidant within the same polymer matrix.

In some embodiments, an equilibrium fluorescence indicator system is located in an internal polymer matrix, wherein one or more exterior coatings around the internal polymer matrix comprise at least one antioxidant. Accordingly, reactive oxygen species are blocked from entering the internal polymer matrix region.

In some embodiments, an internal polymer matrix comprises an equilibrium fluorescence indicator system and one or more antioxidants, and an exterior coating around the internal polymer matrix also comprises at least one antioxidant.

In some embodiments, a semi-permeable membrane is positioned between a polymer matrix and an analyte-containing sample or tissue, wherein the polymer matrix comprises an equilibrium fluorescence indicator system and one or more antioxidant.

In some embodiments, a semi-permeable membrane is positioned between an internal polymer matrix comprising an equilibrium fluorescence indicator system and an exterior coating around the internal polymer matrix comprising at least one antioxidant.

In some embodiments, a semi-permeable membrane is functionalized with or covalently bound to an antioxidant and is positioned between an internal polymer matrix comprising an equilibrium indicator system and the analyte-containing sample or tissue. Non-limiting examples of semi-permeable membranes are porous and nonporous membranes consisting of polyethylene, polypropylene, polyurethane, polyethersulfone, polysulfone, polyacrylonitrile, and cellulose acetate.

In some embodiments, a semi-permeable membrane surrounds an exterior polymer matrix coating comprising at least one antioxidant, wherein the exterior polymer matrix encloses an internal polymer matrix that comprises an equilibrium fluorescence indicator system, wherein the semi-permeable membrane separates the exterior polymer matrix coating from an analyte-containing sample or tissue.

In some embodiments, an equilibrium fluorescence indicator system is located in an internal polymer matrix, wherein an exterior coating around the internal polymer matrix comprises a porous metal or metal oxide coating. The porous metal or metal oxide coating may be applied by various techniques, e.g., by vapor deposition, spraying, sputter coating and precipitation onto a semipermeable membrane.

Analyte Sensors

Analyte sensors disclosed herein are equilibrium fluorescence indicator systems that typically comprise at least an analyte-binding moiety and a fluorophore. When illuminated by light at a particular wavelength, the fluorophore emits detectable light at a longer wavelength (i.e., fluorescence).

In some embodiments, the equilibrium fluorescence indicator systems comprise a quencher with an analyte receptor site. In certain embodiments, when there is no analyte present to bind with the analyte receptor, the quencher prevents the fluorophore system from emitting light when the dye is excited by an excitation light. In certain embodiments, when there is analyte present to bind with the analyte receptor, the quencher allows the fluorophore system to emit light when the dye is excited by an excitation light.

In certain embodiments, the emission produced by the fluorophore system may vary with the pH (as well as the temperature) of the solution (for example, blood), such that different excitation wavelengths (one exciting the acid form of the fluorophore and the other the base form of the fluorophore) produce different emissions signals. In preferred embodiments, the ratio of the emission signal from the acid form of the fluorophore over the emission signal from the base form of the fluorophore is related to the pH level of the blood. In certain embodiments, an interference filter is employed to ensure that the two excitation lights are exciting only one form (the acid form or the base form) of the fluorophore. Chemical indicator systems, hardware configurations and methods for determining both pH and glucose based on ratiometric determination are described in detail in U.S. Pat. No. 7,751,863 and co-pending U.S. application Ser. No. 12/027,158 (published as 2008/0188725); incorporated herein in their entirety by reference thereto.

The indicator system (also referred to herein as a fluorophore system) can comprise a fluorophore operably coupled to a quencher. In certain embodiments, the fluorophore system comprises a polymer matrix comprising a fluorophore susceptible to quenching by a viologen, a viologen quencher with quenching efficacy dependent on glucose concentration, and a glucose permeable polymer, wherein said matrix is in contact with blood in vivo. Preferably the fluorophore is a fluorescent organic dye, the quencher is a boronic acid functionalized viologen, and the matrix is a hydrogel.

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with an analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2NH$—), amide —(C=O)N—, ester —(C=O)—O—, ether —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164, 7,470,420, and 7,751,863, and U.S. Patent Publ. Nos. 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902; each of which is incorporated herein in its entirety by reference thereto.

In accordance with aspects of the present invention, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally cross-linked.

In some embodiments, a moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N'bis-(benzyl)bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorphore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Polymer Matrices

For in vivo applications, the sensor is used in a moving stream of physiological fluid which contains one or more analyte compounds or is implanted in tissue such as muscle which contains said analyte compounds. Therefore, it is preferred that none of the sensing moieties escape from the sensor assembly. Thus, for use in vivo, the sensing components are preferably part of an organic polymer sensing assembly. Soluble dyes and quenchers can be confined by a selectively permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to analyte. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N-dimethyl acrylamide [DMAA], and the like; ionic monomers include methacryloylaminopropyl trimethylammonium chloride, diallyl dimethyl ammonium chloride, vinyl benzyl trimethyl ammonium chloride, sodium sulfopropyl methacrylate, and the like; crosslinkers include ethylene dimethacrylate, PEGDMA, trimethylolpropane triacrylate, N,N'-methylenebisacrylamide, N,N'-methylenebismethacrylamide, and the like. The ratios of monomers are chosen to optimize network properties including permeability, swelling index, and gel strength using principles well established in the art. In one embodiment, the dye moiety is derived from an ethylenically unsaturated derivative of a dye molecule, such as TriCysMA, the quencher moiety is derived from an ethylenically unsaturated viologen such as 3,3'-oBBV and the matrix is made from N,N-dimethyl acrylamide and N,N'-methylenebisacrylamide. The concentration of dye is chosen to optimize emission intensity. The ratio of quencher to dye is adjusted to provide sufficient quenching to produce the desired measurable signal.

In some embodiments, multi-component hydrogels wherein the equilibrium fluorescence indicator system is incorporated in one component and one or more antioxidant components in another are preferred for making the sensor of this invention. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel. By this method, a second hydrogel layer may be added to coat an inner region of hydrogel containing sensor.

The semi-IPN hydrogel is formed by dissolving a soluble polymer containing dye moieties in a mixture of monomers including a quencher monomer that is capable of complex formation with the fluorophore. In some embodiments, the sensing moieties are immobilized by an insoluble polymer matrix which is freely permeable to analyte compounds. Additional details on hydrogel systems have been disclosed in US Patent Publications Nos. US2004/0028612, and 2006/0083688 which are hereby incorporated by reference in their entireties.

Semipermeable Membranes

Semipermeable membranes used in some embodiments of the invention are permeable to the passage of analyte (e.g., glucose) and oxygen. However, they are impermeable to the passage of blood clots, cells, and proteins, and other high molecular weight species in blood.

A semipermeable membrane is preferably an inert, non-toxic material that maintains its integrity when implanted in humans. A suitable biocompatible semipermeable material, to minimize immune reactions and to prevent protein and cell absorption, is preferably selected from the following groups of polymers: polyethylene, polysulfone, cellulose acetate, polyvinyl alcohol, polypropylene, tetraacrylated poly(ethylene glycol) (PEG), and/or polyurethane.

The porosity of the semi-permeable membrane affects both immunoprotection and the selective permeation of molecules. Membrane thickness is important for immunoprotection, as well as for diffusion of analytes. The maximal pore volume fraction and the minimum possible thickness are important to achieve rapid diffusion of analyte and oxygen through the semipermeable membrane. Also, the pore volume fraction, the average pore diameter, and wall thickness affect the mechanical strength of the membrane. Different porosities and thickness (0.01 mm to 0.5 mm) are formed to find the optimal membrane parameters.

Optical Systems for Analyte Detection

Various embodiments of optical systems and methods are disclosed herein for determining blood analyte concentrations. The various embodiments preferably share at least two features. First, they involve exciting a chemical indicator system with an excitation light signal and measuring the emission light signal of the indicator system, wherein the indicator system is in contact with the blood and comprises a fluorescent dye, such that the emission light signal generated by the indicator system upon excitation is related to the blood analyte concentration. Second, they involve correcting the blood analyte concentration measurements from the indicator system for potential artifacts due to the optical system, which artifacts are unrelated to the blood analyte concentration. The correction is performed by ratiometric analysis. More particularly, the ratio of emission light signal to a second light signal that is propagated through the optical system, e.g., the excitation light signal or a separate reference light signal, is used for correcting any non-glucose related contributions of the optical system. Where the excitation light signal is used for the ratiometric correction, the sensor preferably includes a reflective surface, e.g., a mirror, located somewhere along the sensor, such that at least a portion of the excitation light which has passed through the optical system is reflected back to a detector. Where a separate reference light signal is used, the reference light signal may either be: (1) generated by a separate light source and reflected back to a detector, or (2) generated as a separate emission light signal from a separate dye disposed somewhere along the sensor. Thus, an analyte sensor in accordance with preferred embodiments of the present invention will comprise either a reflective surface or a second dye adapted to emit a reference light signal.

Various structural configurations have been proposed for holding a chemical indicator system in a position, which is: (1) exposed to the blood, (2) disposed within the excitation light path, and (3) for exposing a chemical indicator system to the blood and, for introducing to the indicator system an excitation light signal, for detecting an emission light signal from the indicator system, and for enabling ratiometric correction of glucose determinations for artifacts of the system optics; see in particular 2008/0188725. More particularly, aspects of the present invention relate to improvements and alternative embodiments for generating a reference light signal (as discussed in 2008/0188725), either through various mirror/reflective surface configurations adapted to return a portion of the excitation light signal back to a detector or through generating a separate emission light signal from a separate dye. Aspects of the present invention relate to new and improved configurations for disposing a chemical indicator system within an interrogation light path, wherein the sensor is more robust and exhibits improved patient tolerance.

Optical glucose sensors, such as those described in U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617, 12/612,602 and 12/424,902 (each of which is incorporated herein in its entirety by reference thereto) typically employ a chemical indicator system disposed at the distal end of an optical fiber, wherein the indicator system is maintained in contact with the blood, such that an excitation light signal sent distally down the fiber causes the chemical indicator system to emit a light signal related to the concentration of glucose.

In certain embodiments, an optical glucose measurement system is disclosed for measuring glucose concentration in blood using one or more glucose-sensing chemical indicator systems. Such indicator systems preferably comprise a fluorophore operably coupled to a glucose binding moiety. Preferably, the glucose binding moiety acts as a quencher with respect to the fluorophore (e.g., suppresses the fluorescent emission signal of the fluorophore in response to excitation light when it associates with the fluorophore). In preferred embodiments, as the glucose binding moiety binds glucose (e.g., as glucose concentrations rise), it dissociates from the fluorophore, which then generates a fluorescent emission signal upon excitation. Accordingly, in such embodiments, the higher the glucose concentration, the more glucose bound by the binding moiety, the less quenching, and the higher the fluorescence intensity of the fluorophore upon excitation.

In certain embodiments, the optical glucose measurement system measures analyte concentrations intravascularly and in real-time through the use of such chemical indicator systems. In certain embodiments, the analyte-sensing chemical indicator systems are immobilized in a hydrogel. The hydrogel may be inserted into an optical fiber such that light may be transmitted through the hydrogel while at least a portion of the hydrogel is in contact with blood. The hydrogel is preferably permeable to analytes and other low molecular weight moieties present in blood. In certain embodiments, the optical fiber together with the hydrogel comprises an analyte sensor that is placed in a mammalian (human or animal) blood vessel.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902; each of which is incorporated herein in its entirety by reference thereto.

Light may be transmitted into an optical analyte sensor from a light source. In certain embodiments, the light source is a light emitting diode that emits an optical excitation signal. The optical excitation signal excites the fluorophore system(s), such that the fluorophores emit light at an emission wavelength. In certain embodiments, the fluorophore systems are configured to emit an optical emission signal at a first wavelength having an intensity related to the blood analyte concentration in the blood vessel. In certain embodiments, light is directed out of the analyte sensor such that the light is detected by at least one detector. The at least one detector preferably measures the intensity of the optical emission signal, which is related to the analyte concentration present in the blood. Various optical configurations for interrogating analyte-sensing chemical indicator systems with one or more excitation light signals and for detecting one or more emission light signals from the chemical indicator systems may be employed, see e.g., U.S. patent application Ser. No. 12/027,158 (published as 2008/0188725); incorporated herein in its entirety by reference thereto.

In some embodiments, the analyte sensor comprises an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a rod with proximal and distal ends, wherein the proximal end of the rod is attached to the distal end of the optical fiber, and wherein the distal end of the rod is attached to the proximal end of the atraumatic tip portion, such that the rod traverses the gap and couples the optical fiber to the atraumatic tip portion; a chemical indicator system capable of generating an emission light signal in response to an excitation light signal, wherein the intensity of the emission light signal is related to the analyte concentration, and wherein the chemical indicator system is disposed within the gap; and a selectively permeable membrane disposed over the gap, wherein the sensor is sized for deployment within a blood vessel.

In one variation to the analyte sensor, the chemical indicator system is immobilized within the gap by a hydrogel. In another variation, the sensor further comprises a temperature sensor. The optical fiber preferably has a diameter of between about 0.005 inches and about 0.020 inches. In another variation, the sensor further comprises a reflective region. Preferably, the reflective region comprises a reflective surface on the proximal end of the rod. In one embodiment, the rod may be attached to the optical fiber and atraumatic tip portion by heating. In another embodiment, the rod may be attached to the optical fiber by a reflective or optically clear adhesive.

In variations to the sensor, the shape of the distal end of the atraumatic tip portion may be configured to reduce trauma within the blood vessel. In various embodiments, the shape of the distal end of the atraumatic tip portion may be selected from the group consisting of hemispherical, parabolic, and elliptical. In another variation, the distal end of the atraumatic tip portion is flexible. In another variation, the distal end of the atraumatic tip portion is deformable. The distal end of the atraumatic tip portion may be formed from at least one material selected from the group consisting of plastics, polymers, gels, metals and composites.

In some embodiments, the sensor comprises an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a hypotube with proximal and distal ends, wherein the proximal end of the hypotube is attached to the distal end of the optical fiber, and wherein the distal end of the hypotube is attached to the proximal end of the atraumatic tip portion, such that the hypotube traverses the gap and couples the optical fiber to the atraumatic tip portion, wherein the hypotube comprises at least one window that opens onto the gap; a chemical indicator system capable of generating an emission light signal in response to an excitation light signal, wherein the intensity of the emission light signal is related to the analyte concentration, and wherein the chemical indicator system is disposed within the gap; and a selectively permeable membrane disposed over the at least one window, wherein the sensor is sized for deployment within the blood vessel. In preferred embodiments, the chemical indicator system is immobilized by a hydrogel within the cavity formed within the hypotube. In further preferred embodiments of the sensor with hypotube, a reflective member is disposed within the sensor. In further preferred embodiments of the sensor with hypotube, a fluorescent member is disposed within the sensor.

In other embodiments, the sensor comprises: an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a cage connecting the optical fiber and atraumatic tip portion, wherein the optical fiber is at least partially enclosed within the cage, and wherein the cage has at least one window; a chemical indicator system disposed within the cage, wherein the chemical indicator system is adjacent the window and is separated from analyte by a selectively permeable membrane, and wherein the chemical indicator system is capable of generating an emission light signal in response to an excitation light signal, wherein the intensity of the emission light signal is related to the analyte concentration; and a reference material, wherein the reference material is configured to either reflect a portion of the excitation light signal before the excitation light signal enters the chemical indicator system or to return a second emission light signal, wherein the intensity of the second emission light signal is not related to the analyte concentration.

Electrochemical sensors based on glucose oxidase are known to be subject to sensor drift over time. Such sensors may have one level of glucose response initially, then another level of glucose response subsequently. The drift of electrochemical sensors has been a major factor in their design and development, confounding efforts to provide a prospective calibration for the devices and necessitating frequent recalibration to compensate for such effects. The problem of electrochemical sensor drift was recently discussed by Brauker (Brauker J Continuous Glucose Sensing: Future Technology Developments, DIABETES TECHNOLOGY & THERAPEUTICS, Volume 11, Supplement 1, 2009, S25-S36), which states:

"Sensors measure glucose accurately and reproducibly on the bench with no more need for calibration than that required of a meter. The difference is that a continuous sensor is placed into the body, within a needle track wound that changes dramatically over the course of the hours and days following implantation. The ever-changing wound healing environment produces high variability of glucose and oxygen in the wound site. The glucose in the region is always proportionate to the glucose in the blood, but the ratio of glucose at the sensor interface to glucose in the blood changes over time because of varying utilization by cells as the wound healing process advances. These changes create the necessity for ongoing calibration changes. It is this calibration process that contributes the most error to sensors."

An additional explanation for the well-known drift problem with electrochemical sensors may be the presence of endogenous sources of hydrogen peroxide associated with the inflammatory response of the body to the sensor material and insertion process. Since electrochemical sensors rely on the detection of hydrogen peroxide produced by the glucose oxidase reaction, these sensors are subject to erroneous measurement when exposed to endogenous sources of hydrogen peroxide. The use of enzymes such as catalase or glutathione peroxidase, as well as silver or silver nanoparticles, could reduce the exposure of electrochemical sensors to endogenous sources of hydrogen peroxide, thereby reducing or eliminating a potentially significant source of error on those devices.

EXAMPLE 1

Sensor Containing Fluorescence Indicator System and Antioxidant

A hydrogel is prepared to which an equilibrium fluorescence indicator system and one or more antioxidant is covalently bonded. The hydrogel is formed by free radical copolymerization of a mixture of hydrophilic monomers and crosslinker in the presence of the equilibrium fluorescence indicator system. The sensing hydrogel is transferred to a fresh solution of PBS and the fluorescence intensity of the equilibrium fluorescence indicator system is monitored over time. The PBS solution is replaced with an analyte solution in pH 7.4 PBS and a fluorescence increase is monitored. The analyte solution is spiked with a reactive oxygen species and the sensor is allowed to be in contact with the reactive oxygen species. The reactive oxygen species solution is replaced with a fresh analyte solution and the fluorescence intensity monitored over time.

EXAMPLE 2

Interpenetrating Polymer Network (IPN)

A hydrated sensor containing an equilibrium fluorescence indicator system polymerized in a hydrogel is immersed in a monomer solution (130 µL) containing DMAA, (10% v/v), N,N'-methylenebisacrylamide (2% w/w of DMAA), one or more antioxidants, ammonium persulfate (0.3%), and PBS (90% v/v, 20 mM, pH 7.0). After 2 h, TEMED (50 µL, 10% in pH 7.0 PBS) is added and the mixture is allowed to polymerize over 2 h at room temperature. The sensor is withdrawn from the bulk hydrogel polymer and leached in pH 7.4 PBS for 15 h. The sensor is transferred to a fresh solution of PBS and its fluorescence intensity is monitored over time at 37° C. The PBS solution is replaced with an analyte solution in pH 7.4 PBS and the fluorescence increase is monitored. The analyte solution is spiked with a reactive oxygen species and the sensor is allowed to be in contact with the reactive oxygen species. The reactive oxygen species solution is replaced with a fresh analyte solution and the fluorescence intensity monitored over time.

EXAMPLE 3

Figure 2:
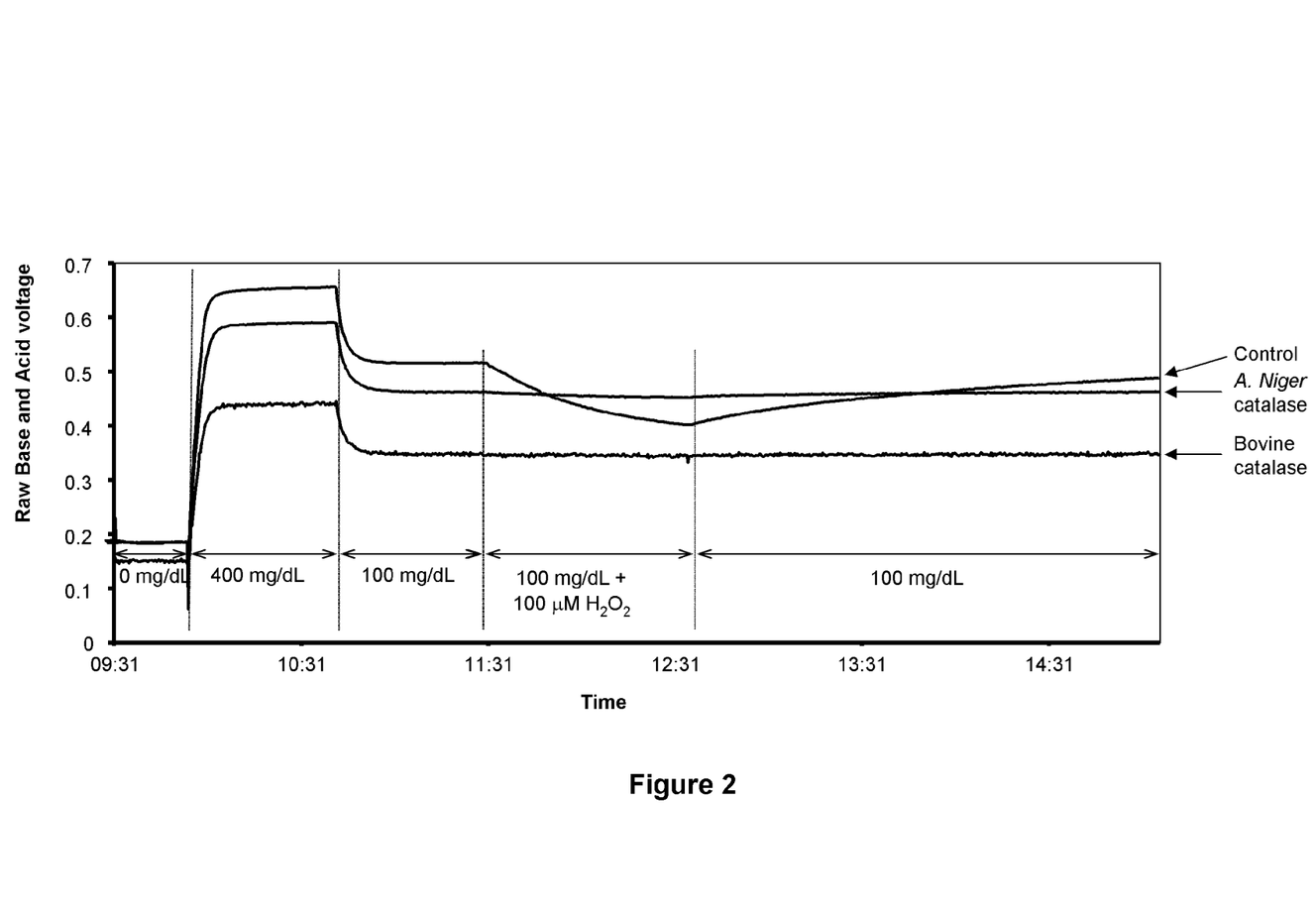
FIG. 2. Comparison of catalase-protected sensors upon addition of 100 μM $H_2O_2$.

IPN Containing TriCysMA and 3,3'-oBBV with External Coating Containing Catalase A hydrated sensor containing polymerized TriCysMA and 3,3'-oBBV was immersed in a monomer solution (130 µL) containing DMAA, (10% v/v), N,N'-methylenebisacrylamide (2% w/w of DMAA), bovine catalase (0.3%, activity=14000 U/mg protein) or *Aspergillus niger* catalase (0.3%, activity=20,000 U/mg protein), ammonium persulfate (0.3%), and PBS (90% v/v, 20 mM, pH 7.0) After 2 h, TEMED (50 µL, 10% in pH 7.0 PBS) was added and the mixture was allowed to polymerize over 2 h at room temperature. The sensor was withdrawn from the bulk hydrogel polymer and leached in pH 7.4 PBS for 15 h. The sensor was transferred to a fresh solution of PBS and its fluorescence intensity was monitored over time. The PBS solution was replaced with a 400 mg/dL glucose solution in pH 7.4 PBS and the fluorescence increase was monitored. The glucose solution was replaced with a different concentration glucose solution (100 mg/dL) and the fluorescence decrease was monitored. The glucose solution was spiked with $H_2O_2$ (100 µM) and the sensors were allowed to be in contact with the $H_2O_2$ for 30 minutes. The $H_2O_2$ solution was replaced with a fresh glucose solution (100 mg/dL) and the fluorescence intensity monitored over time. As illustrated in FIG. 24, the sensors protected with catalase hydrogel did not degrade in the presence of $H_2O_2$, while those that did not contain catalase did degrade, giving a characteristic "dip and rise" in signal intensity.

EXAMPLE 4

Sensor Containing Fluorescence Indicator System and Antioxidant with External Coating Containing Additional Antioxidant A hydrated sensor containing an equilibrium fluorescence indicator system and one or more antioxidants is polymerized in a hydrogel. The hydrogel containing the equilibrium fluorescence indicator system and one or more antioxidants is immersed in a monomer solution (130 µL) containing DMAA, (10% v/v), N,N'-methylenebisacrylamide (2% w/w of DMAA), one or more antioxidants, ammonium persulfate (0.3%), and PBS (90% v/v, 20 mM, pH 7.0). After 2 h, TEMED (50 µL, 10% in pH 7.0 PBS) is added and the mixture is allowed to polymerize over 2 h at room temperature. The sensor is withdrawn from the bulk hydrogel polymer and leached in pH 7.4 PBS for 15 h. The sensor is transferred to a fresh solution of PBS and its fluorescence intensity is monitored over time at 37° C. The PBS solution is replaced with an analyte solution in pH 7.4 PBS and the fluorescence increase is monitored. The analyte solution is spiked with a reactive oxygen species and the sensor is allowed to be in contact with the reactive oxygen species. The reactive oxygen species solution is replaced with a fresh analyte solution and the fluorescence intensity monitored over time.

EXAMPLE 5

IPN Containing TriCysMA with External Coating Containing Trolox or Catalase/Trolox Combination

Figure 3:
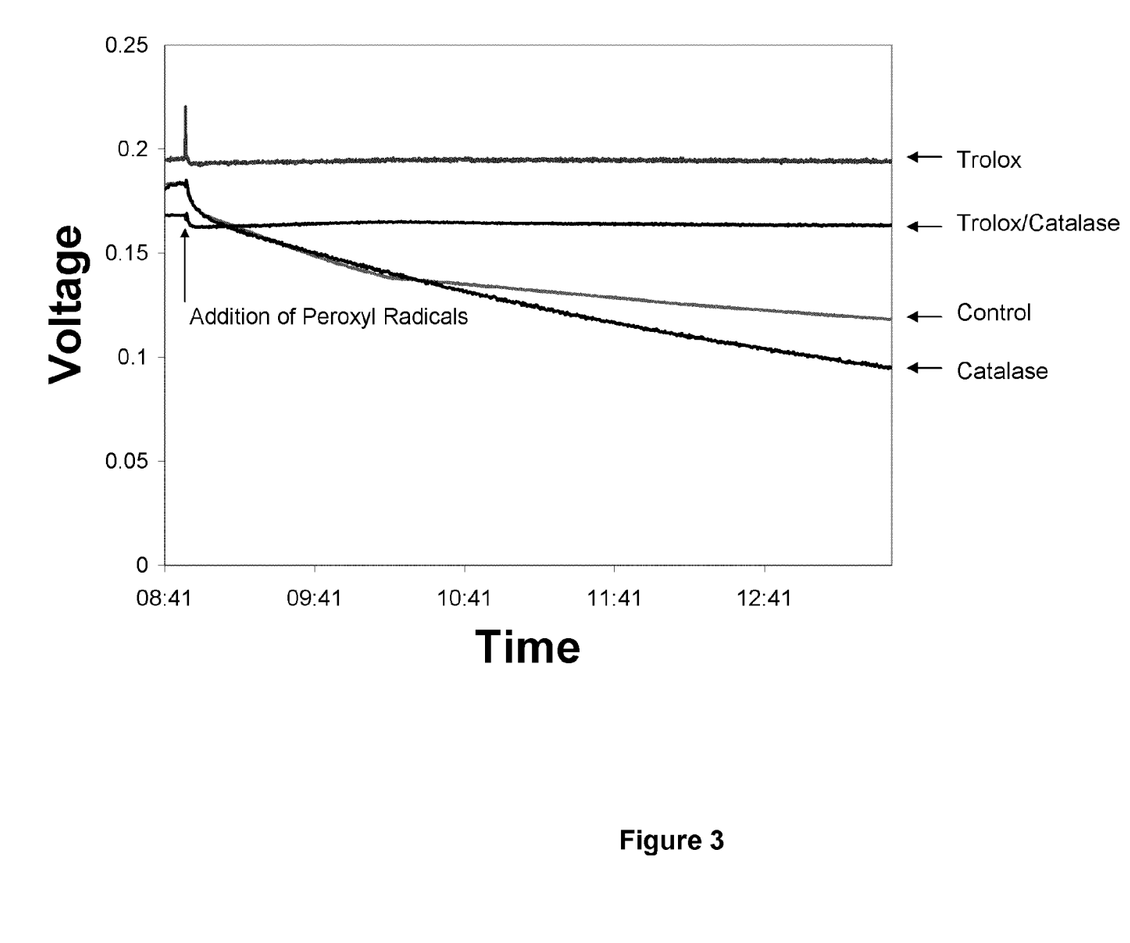
FIG. 3. Dye only sensors with protected hydrogel after addition of peroxyl radicals.

A hydrated sensor containing polymerized TriCysMA was immersed in a monomer solution (130 µL) containing DMAA, (10% v/v), N,N'-methylenebisacrylamide (2% w/w of DMAA), Trolox derivative (20 mg/mL), ammonium persulfate (0.3%), and PBS (90% v/v, 20 mM, pH 7.0). After 2 h, TEMED (50 µL, 10% in pH 7.0 PBS) was added and the mixture was allowed to polymerize over 2 h. The sensor was withdrawn from the bulk hydrogel polymer and leached in pH 7.4 PBS for 15 h. The sensor was transferred to a fresh solution of PBS and its fluorescence intensity was monitored over time at 37° C. The PBS solution was spiked with 2,2'-Azobis[2-(2-imidazolin-2-yl)propane]dihydrochloride to give a final concentration of 10 mM and the sensors were allowed to be in contact with the free radical source for 5 h while the fluorescence intensity was monitored over time. As illustrated in FIG. 3, the sensors protected with the Trolox derivative did not degrade in the presence of free radicals, while those that did not contain Trolox did degrade, giving a drop in signal intensity.

EXAMPLE 6

Covalent Immobilization of Catalase on Membrane

Reaction:
Catalase was attached to a high density polyethylene microporous membrane (HDPE MPM) as follows:

Procedure:
Stock solutions of pH 5 MES (0.1M MES, 0.5M NaCl), Boc-amido-dPEG$_4$-acid (5 mL of 0.1 M), NHS (5 mL of 0.2 M in pH 5 IVIES, catalase (10 mL of 10 mg/mL in pH 5 MES) and EDC (5 mL of 0.2 M in pH 5 MES) were prepared and stored at 4° C.

Boc-amido-dPEG$_4$-acid (1.2 mL, 0.1 M), NHS (1.2 mL, 0.2M), and EDC (1.2 mL, 0.2M) were added to a 4-mL vial at 4° C. and stored for 15 min. Six 1-cm pieces of ammonia-plasma-treated microporous membrane (MPM) were placed in the vial and allowed to react for 15 h at 4° C. The excess reagents were removed and the MPMs were washed with water (3×4 mL). The MPMs were stirred in 0.275M HCl in 70% EtOH/H$_2$O in a scintillation vial for 3 h. The excess reagents were removed and the MPMs were washed with water (3×4 mL). In a separate 4-mL vial, catalase (1.2 mL, 10 mg/mL), NHS (1.2 mL, 10 mM) and EDC (1.2 mL, 10 mM) were added and the vial was stored at 4° C. for 15 min. Six PEGylated, deprotected MPMs were added to the 4-mL vial and it was stored at 4° C. for 15 h. The excess reagents were removed and the catalase activity was measured using a KMnO$_4$/H$_2$O$_2$ titration assay.

The activity of the catalase on the PEG-membrane was compared to membrane treated with catalase but with no coupling agents.

| Catalase Activities | |
|---|---|
| Sample Type | μM H$_2$O$_2$/min |
| PEG-MPM | 127.50 |
| Control MPM | 28.89 |

The assay reveals that microporous membrane treated with PEG and coupling agents has higher activity than the control, which contained no coupling agents. This represents an effective method for covalently attaching catalase to the surface of a microporous membrane.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. An analyte sensor, comprising an equilibrium fluorescence indicator system and at least one antioxidant, wherein each of the equilibrium fluorescence indicator system and the at least one antioxidant are immobilized within a polymer matrix, wherein said equilibrium fluorescence indicator system comprises a fluorophore operably coupled to a glucose binding moiety functionalized with boronic acid, wherein the equilibrium fluorescence indicator system provides a fluorescence signal intensity related to glucose concentration, and wherein the equilibrium fluorescence indicator system is protected by said at least one antioxidant against degradation caused by hydrogen peroxide such that a presence of the hydrogen peroxide provides no change in the fluorescence signal intensity related to glucose concentration.

2. The analyte sensor of claim 1, wherein the equilibrium fluorescence indicator system and the at least one antioxidant is immobilized within a common polymer matrix.

3. The analyte sensor of claim 1, wherein the equilibrium fluorescence indicator system is immobilized within a first polymer matrix and the at least one antioxidant is immobilized within a second polymer matrix that forms an exterior coating around the first polymer matrix.

4. The analyte sensor of claim 2, further comprising a second polymer matrix that comprises at least one antioxidant, wherein said second polymer matrix forms an external coating around the common polymer matrix within which the equilibrium fluorescence indicator system and the at least one antioxidant are immobilized.

5. The analyte sensor of claim 1, wherein the at least one antioxidant is selected from the group consisting of a catalytic antioxidant, a scavenger and a synthetic antioxidant.

6. The analyte sensor of claim 5, wherein the catalytic antioxidant is selected from the group consisting of catalase (CAT), glutathione peroxidase (GSH-Px), and selenium glutathione peroxidase.

7. The analyte sensor of claim 5, wherein the catalytic antioxidant is selected from the group consisting of bioconjugates of catalase (CAT), glutathione peroxidase (GSH-Px) and selenium glutathione peroxidase.

8. The analyte sensor of claim 5, wherein the synthetic antioxidant is TEMPOL.

9. The analyte sensor of claim 5, wherein the scavenger antioxidant is selected from the group consisting of vitamin A, a retinol, a carotenoid, a limonoid, a phytosterol, a flavonoid, an anthocyanidin, a catechin, an isoflavone, an oligomeric proanthocyanidin, an isothiocyanate, a dithiolthione, a sulforaphane, an isoprenoid, a tocotrienol, a tocopherol, vitamin E, lipoic acid, ubiquinone, an ascorbate, vitamin C, 2,3-dihydro-1-benzofuran-5-ols, a chromanone, a water-soluble fullerene antioxidant, C60, C70, a phenolic antioxidant compound, butylated hydroxytoluene (BHT), Trolox™, a polyphenolic antioxidant compound, caffeic acid, hydrocaffeic acid, vanillic acid, cinnamic acid, benzoic acid and pyruvate.

10. The analyte sensor of claim 5, wherein the synthetic antioxidant is a porphyrin-based synthetic antioxidant.

11. The analyte sensor of claim 5, wherein the synthetic antioxidant is a noble metal selected from the group consisting of platinum, palladium, silver, gold, and alloys thereof or a metal oxide or sulfide selected from the group consisting of manganese dioxide, ruthenium oxide, ruthenium sulfide, and silver oxide.

12. The analyte sensor of claim 11, wherein the synthetic antioxidant is in the form of a porous coating or in the form of colloidal particles or nanoparticles of silver oxide, or nanoparticles of platinum, silver, or gold.

13. The analyte sensor of claim 1, wherein the at least one antioxidant comprises a cocktail of two or more antioxidants.

14. The analyte sensor of claim 13, wherein said two or more antioxidants are a catalase and an antioxidant phenolic compound.

15. The analyte sensor of claim 14, wherein said antioxidant phenolic compound is Trolox™ or a Trolox™ derivative.

16. The analyte sensor of claim 13, wherein said two or more antioxidants are a catalase enzyme and vitamin E.

17. The analyte sensor of claim 3, wherein the first and second polymer matrices are physically separated by a semipermeable membrane.

18. The analyte sensor of claim 1, wherein the equilibrium fluorescence indicator system comprises:
   a fluorescent, organic dye;
   a boronic acid functionalized viologen quencher;
   and a hydrogel matrix.

* * * * *